(12) United States Patent
Collins et al.

(10) Patent No.: US 8,380,297 B2
(45) Date of Patent: Feb. 19, 2013

(54) SYSTEM FOR MEASURING A USER'S PERCENTAGE OF BODY FAT

(76) Inventors: John Collins, Monrovia, CA (US); Colin Kenneth Hill, San Dimas, CA (US)

( * ) Notice: Subject to any disclaimer, the term of this patent is extended or adjusted under 35 U.S.C. 154(b) by 345 days.

(21) Appl. No.: 12/781,164

(22) Filed: May 17, 2010

(65) Prior Publication Data

US 2011/0282235 A1    Nov. 17, 2011

(51) Int. Cl.
*A61B 5/00* (2006.01)
(52) U.S. Cl. ....................................... 600/547
(58) Field of Classification Search ................... 600/547
See application file for complete search history.

(56) References Cited

U.S. PATENT DOCUMENTS

| | | | | |
|---|---|---|---|---|
| 5,372,141 A | * | 12/1994 | Gallup et al. | 600/547 |
| 5,788,643 A | * | 8/1998 | Feldman | 600/506 |
| 2005/0033127 A1 | * | 2/2005 | Ciurczak et al. | 600/316 |
| 2005/0192488 A1 | * | 9/2005 | Bryenton et al. | 600/301 |
| 2008/0086058 A1 | * | 4/2008 | Chamney et al. | 600/547 |
| 2008/0234600 A1 | * | 9/2008 | Marsh | 600/549 |
| 2009/0043222 A1 | * | 2/2009 | Chetham | 600/547 |
| 2010/0081960 A1 | * | 4/2010 | McKenna | 600/547 |

* cited by examiner

*Primary Examiner* — Max Hindenburg
(74) *Attorney, Agent, or Firm* — Wood, Phillips, Katz, Clark & Mortimer

(57) ABSTRACT

A system for measuring percentage of body fat for a user. The system has: structure for measuring body hydration and generating a signal representing a measured hydration value; structure for selectively changing the measured hydration value to an adjusted hydration value based upon a first parameter to thereby reflect more accurately an actual hydration value for the user and generating a signal representing the adjusted hydration value; and structure for measuring body fat percentage using the signal representing: a) the measured hydration value; or b) the adjusted hydration value in the event that the structure for selectively changing the measured hydration value changes the measured hydration value based upon the first parameter.

20 Claims, 5 Drawing Sheets

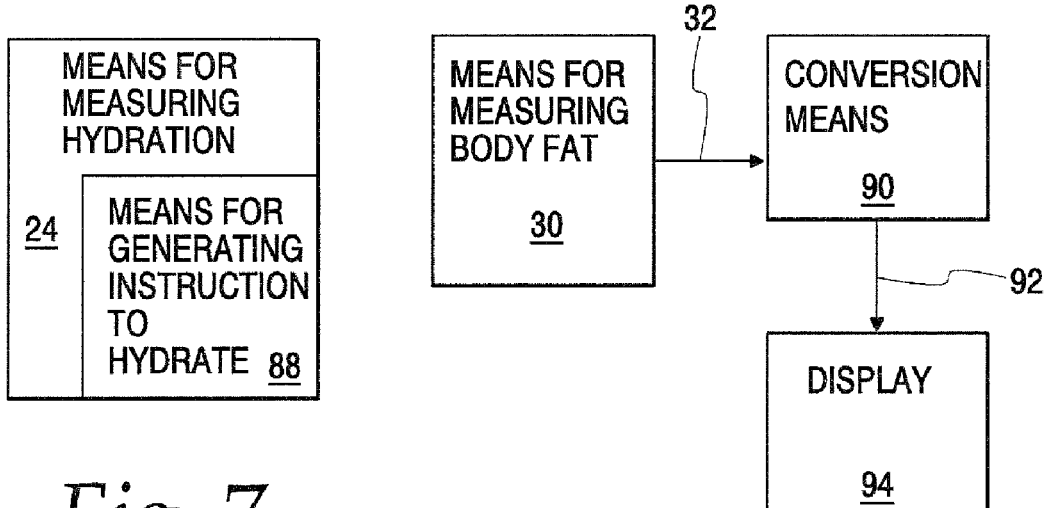
*Fig. 7*
*Fig. 8*
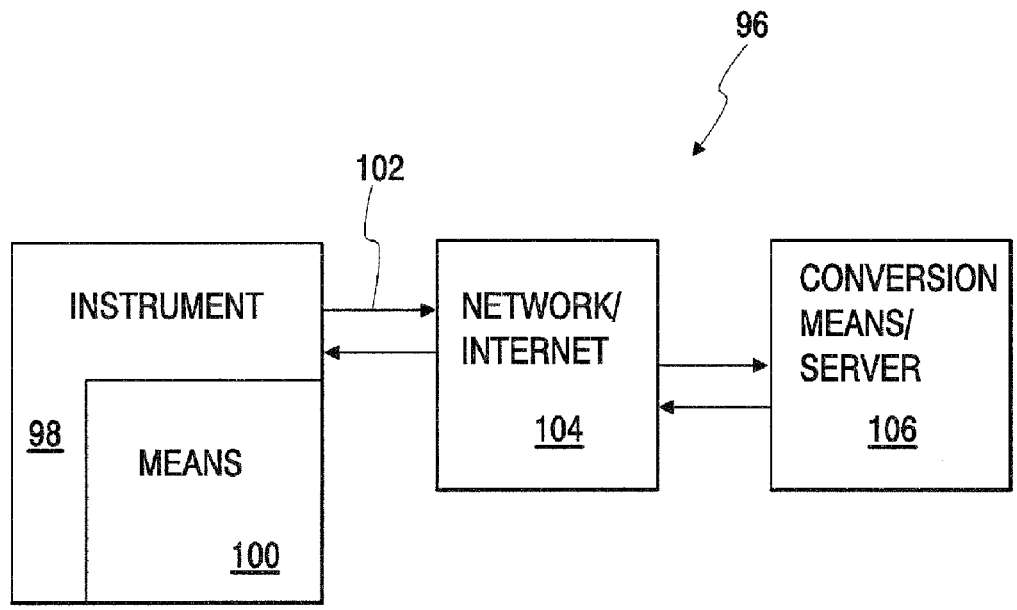
*Fig. 9*

SYSTEM FOR MEASURING A USER'S PERCENTAGE OF BODY FAT

BACKGROUND OF THE INVENTION

1. Field of the Invention

This invention relates to human body composition and, more particularly, to a system for measuring a user's body fat percentage taking into consideration hydration levels.

2. Background Art

Individuals and businesses worldwide are becoming increasingly interested in maintaining human health. From a business perspective, healthy employees are generally more productive and reliable. Preventable illnesses that result in employee down time are placing a greater strain on productivity requirements and the healthcare obligations of businesses for their employees. This problem is in addition to that of "covering" for employees during short or extended absences.

From an individual standpoint, good health contributes not only to longevity, but a more productive and enjoyable life.

With the increasing emphasis on health maintenance, technology has been evolving that allows individuals to more effectively monitor critical health parameters, among which is body fat percentage, a key indicator of overall health level. A multitude of instruments have been devised based upon bioimpedance technology, which relies upon the ability to measure resistance to a low level electrical signal introduced into the body at one location and received at another.

The assignee herein has developed a line of technology including bioimpedance instrumentation wherein an electrical signal is introduced through the user's one hand and received through the user's other hand. Exemplary technology is shown in applicant's pending application Ser. No. 10/882,139 entitled "Method and System for Evaluating A Cost For Health Care Coverage For An Entity", the disclosure of which is incorporated herein by reference.

Generally, resistance is measured in ohms, with the applicant's commercial products having an ohms bridge allowing from 100-1100 ohms. The higher the ohms, the higher is the resistance. An ohms reading is then incorporated into an individual profile including age, weight, gender, height, and athletic activity. A person may be categorized and measurements derived therefor based upon whether the person is, for example, sedentary, inactive, active, athletic, a professional athlete, a bodybuilder, etc.

The low level electrical signals in this type of instrumentation pass through the body through any conductive material. In the human body, the most conductive route is water, that is contained within lean muscle, bone marrow, blood, main organs such as the bladder, etc. Water is not contained within fat.

Resistance measurement in the human body will also be affected by the level of hydration. If a user is underhydrated, the ohms reading/resistance will be higher. When this resistance value is processed through a bioimpedance device, the calculated body fat percentage will be artificially elevated, potentially as much as five percent or higher.

As this technology evolves, it is becoming more and more important that, for any meaningful reliance on calculated body fat percentage values, the accuracy be maintained so that there is a limited percentage error. The failure to take into account underhydration or dehydration may result in body fat percentage measurements that are significantly inaccurate and that may vary from one measurement to the next based upon fluctuation in hydration for the user.

The industry continues to seek out instrumentation that is affordable yet accurate to the point that health attributes can be accurately quantified and monitored to assist lifestyle selections that will improve and/or maintain users' overall health.

SUMMARY OF THE INVENTION

In one form, the invention is directed to a system for measuring percentage of body fat for a user. The system includes: structure for measuring body hydration and generating a signal representing a measured hydration value; structure for selectively changing the measured hydration value to an adjusted hydration value based upon a first parameter to thereby reflect more accurately an actual hydration value for the user and generating a signal representing the adjusted hydration value; and structure for measuring body fat percentage using the signal representing: a) the measured hydration value; or b) the adjusted hydration value in the event that the structure for selectively changing the measured hydration value changes the measured hydration value based upon the first parameter.

In one form, the structure for selectively changing the measured hydration value includes structure for automatically changing the measured hydration value to an adjusted hydration value based upon the first parameter.

In one form, the first parameter is a preset minimum hydration value and the structure for selectively changing the measured hydration value includes structure for changing the measured hydration value to the preset minimum hydration value in the event that the measured hydration value is below the preset minimum hydration value.

In one form, the structure for measuring body hydration includes structure for notifying the user that the user is not properly hydrated in the event that the measured hydration value is below the preset minimum hydration value.

In one form, the preset minimum hydration value is based upon a conventional adequate hydration value derived from a general population analysis.

In one form, the preset minimum hydration value is a baseline hydration value derived from a plurality of prior hydration measurements used by the structure for measuring body fat percentage for the user.

In one form, the baseline hydration value is derived by using at least two prior hydration values for the user used by the structure for measuring body fat percentage.

In one form, the two prior hydration values are successive hydration values used by the structure for measuring body fat percentage.

In one form, the baseline hydration value is derived by averaging a plurality of prior hydration values used by the structure for measuring body fat percentage.

In one form, the baseline hydration value is derived by averaging at least two and less than all prior hydration values from a collection of prior hydration values used by the structure for measuring body fat percentage in the collection of prior hydration values.

In one form, the system further includes a display for identifying user body fat percentage as measured by the structure for measuring body fat in a human readable form.

In one form, the structure for measuring body fat percentage generates a signal in non-human readable form representing measured body fat percentage and the system further includes a conversion structure for changing the signal representing body fat percentage from non-human readable form into a human readable form.

In one form, the structure for measuring hydration, structure for measuring body fat, and display are at a first location and the conversion structure is at a second, remote location.

In one form, the structure for measuring hydration, structure for measuring body fat, and display are all at the same location.

In one form, the signal representing measured body fat percentage is conveyed to the conversion structure over one of a local area network or the internet.

In one form, the structure for measuring hydration, structure for measuring body fat, and display are combined into an instrument at the first location.

In one form, the first parameter is a preset minimum hydration value and the structure for measuring body hydration includes structure for notifying a user that the user is not properly hydrated as indicated by the fact that a measured hydration value is below the preset minimum hydration value and thereafter sending a signal to the structure for measuring body fat percentage only after the structure for measuring body hydration has generated a signal representing a second measured hydration value and after the user has been notified that the user is not properly hydrated.

In one form, the structure for selectively changing the measured hydration value includes structure for generating a signal representing the measured hydration value used by the structure for measuring body fat percentage in the event that the measured hydration value exceeds the baseline hydration value.

In one form, the structure for measuring body fat percentage includes structure for measuring body fat percentage based upon a measured electrical resistance.

In one form, the preset minimum hydration value is on the order of 75%.

BRIEF DESCRIPTION OF THE DRAWINGS

FIG. 7 is a schematic representation of a means on the system in FIG. 2 for measuring hydration and including a means for generating instructions to a user to hydrate under appropriate conditions;

FIG. 8 is a schematic representation of a means for measuring body fat on the system in FIG. 2 that produces a signal representative of the calculated body fat percentage that is communicated to a conversion means to allow display of a fat percentage value; and FIG. 9 is a schematic representation of the inventive system as operated on a local area network or over the internet.

DETAILED DESCRIPTION OF THE PREFERRED EMBODIMENT

Figure 1:
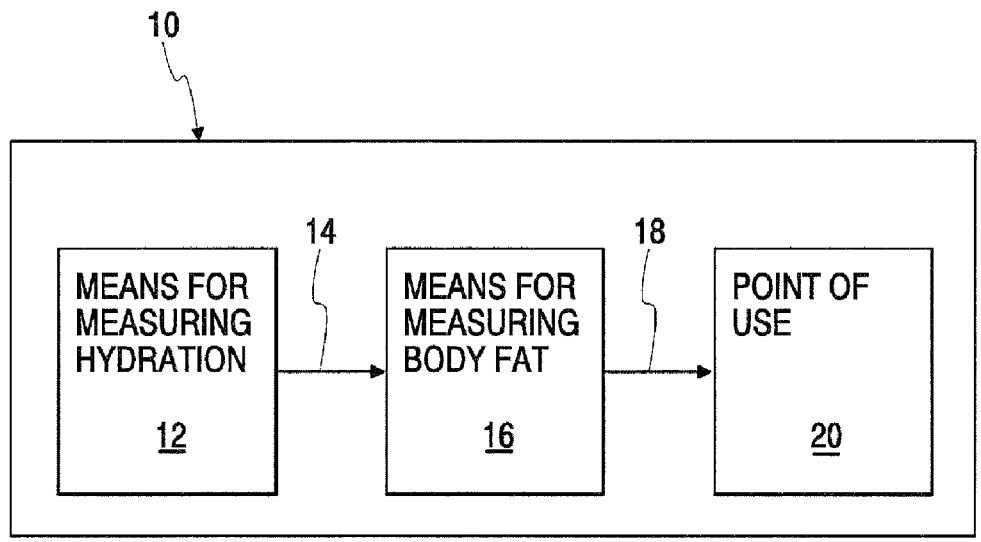
FIG. 1 is a schematic representation of a conventional system for measuring percentage of body fat for a user.

In FIG. 1, a conventional system for measuring percentage of body fat for a user is shown at 10. The system 10 consists of a means for measuring hydration at 12, using well-known technology. The means 12 generates a signal 14 that is processed by a means for measuring body fat 16, that in turn produces a signal 18 representing the user's body fat percentage. That signal 18 is directed to a point of use 20, that might be a display or another device configured to further process or store signals.

Figure 2:
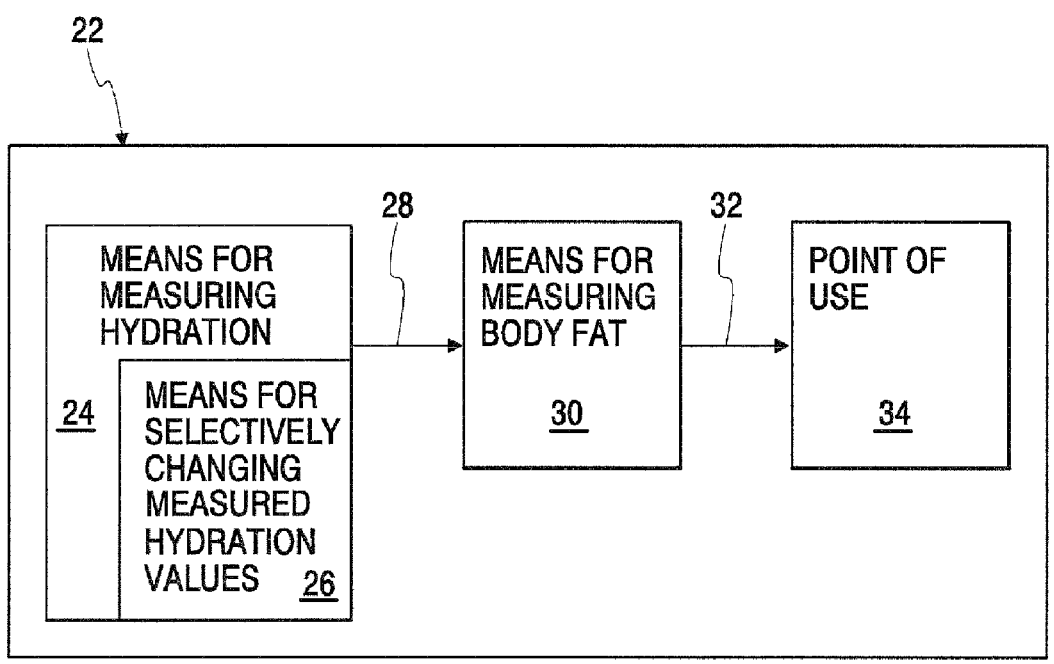
FIG. 2 is a schematic representation of the inventive system for measuring percentage of body fat for a user.

In FIG. 2, a system for measuring percentage of body fat for a user, according to the invention, is shown schematically at 22. The system 22 consists of a means for measuring hydration at 24, which incorporates a means for selectively changing measured hydration values at 26. As explained in greater detail below, the means 26 may be operable automatically to change a measured hydration value to an adjusted hydration value based upon a particular parameter, as also described below.

The means 24 generates a signal 28 that is representative of either the measured or adjusted hydration value. The signal 28 is directed to a means for measuring body fat 30. The means 30 processes the signal 28, and other input data for the user, and generates a signal 32 representing a percentage body fat measurement for the user. The signal 32 is directed to a point of use 34, that might be a display at the user site or a display at a remote location. Alternatively, the point of use 34 might be a device wherein the signal 32 is further processed, converted, stored, or otherwise manipulated.

The system 22 and its components are shown schematically since the precise configuration of each is not critical to the present invention. As noted above, exemplary usable technology is disclosed in applicant's pending application Ser. No. 10/882,139, entitled "Method and System for Evaluating A Cost for Health Care Coverage for an Entity", which is incorporated herein by reference. The schematic showing of these components is intended to encompass virtually every conceivable variation of the basic technology that is required to perform as herein described. Those skilled in the art could devise myriad variations of these components with different capabilities, yet all with the ability to perform the basic functions contemplated by the invention.

The function and significance of the means 26 will now be described. Medical studies and researchers have shown that the average percentage of water within lean body mass is 75%. Hydration ranges can generally be classified as follows:

Optimum—80%-85%;
Good—75%-80%;
Adequate—70%-75%;
Marginal—65%-70%;
Inadequate—60%-65%; and
Poor—below 60%.

When the hydration of lean mass is below 75%, false high readings of body fat may become significant.

Figure 3:
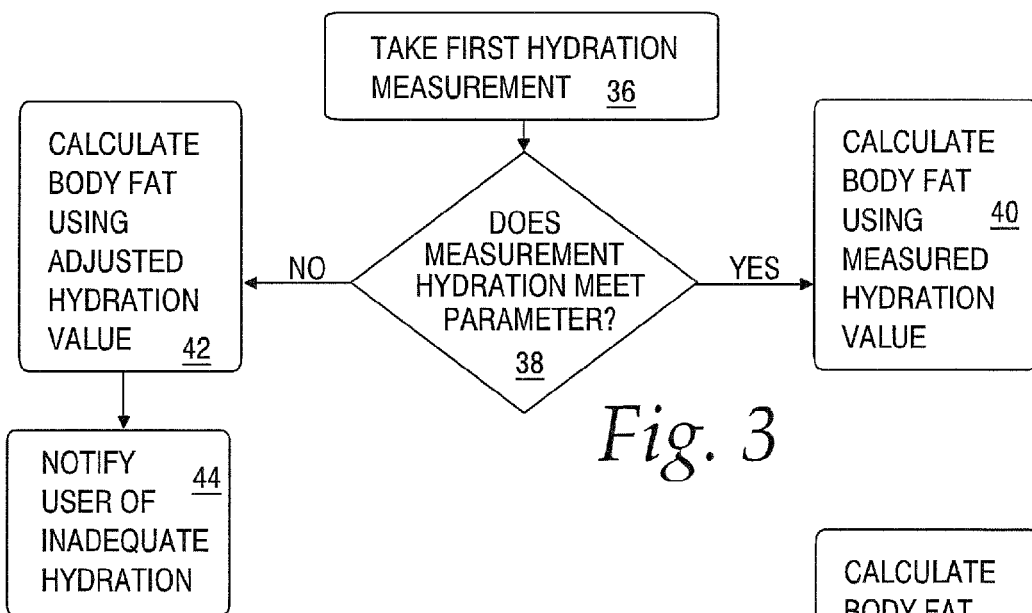
FIG. 3 is a flow diagram representation of a process for measuring body fat percentage for a user with the system in FIG. 2 based upon a first hydration value.

As shown in flow diagram form in FIG. 3, using the system 22, a first hydration measurement is taken using the means 24, as shown at block 36. As shown at block 38, the means 24, through the means 26, determines whether the first measured hydration value meets an established parameter. While the parameter may vary, one exemplary parameter is a pre-set minimum hydration value, which for purposes of example will be 75% or another value based upon recognized adequate hydration values derived from a general population analysis. If it is determined that a first measured hydration value is at or above 75%, that value will be used by the means 30 to calculate the user's body fat percentage, as shown at block 40.

If the first measured hydration value is below 75%, the user's body fat measurement will be calculated through the means 30 using an adjusted hydration value of 75%, as shown at block 42. Additionally, the system 22 is configured to notify the user of inadequate hydration as evidenced by the first measured hydration value, as shown at block 44. This notification may be generated by the means 24, or otherwise.

Figure 4:
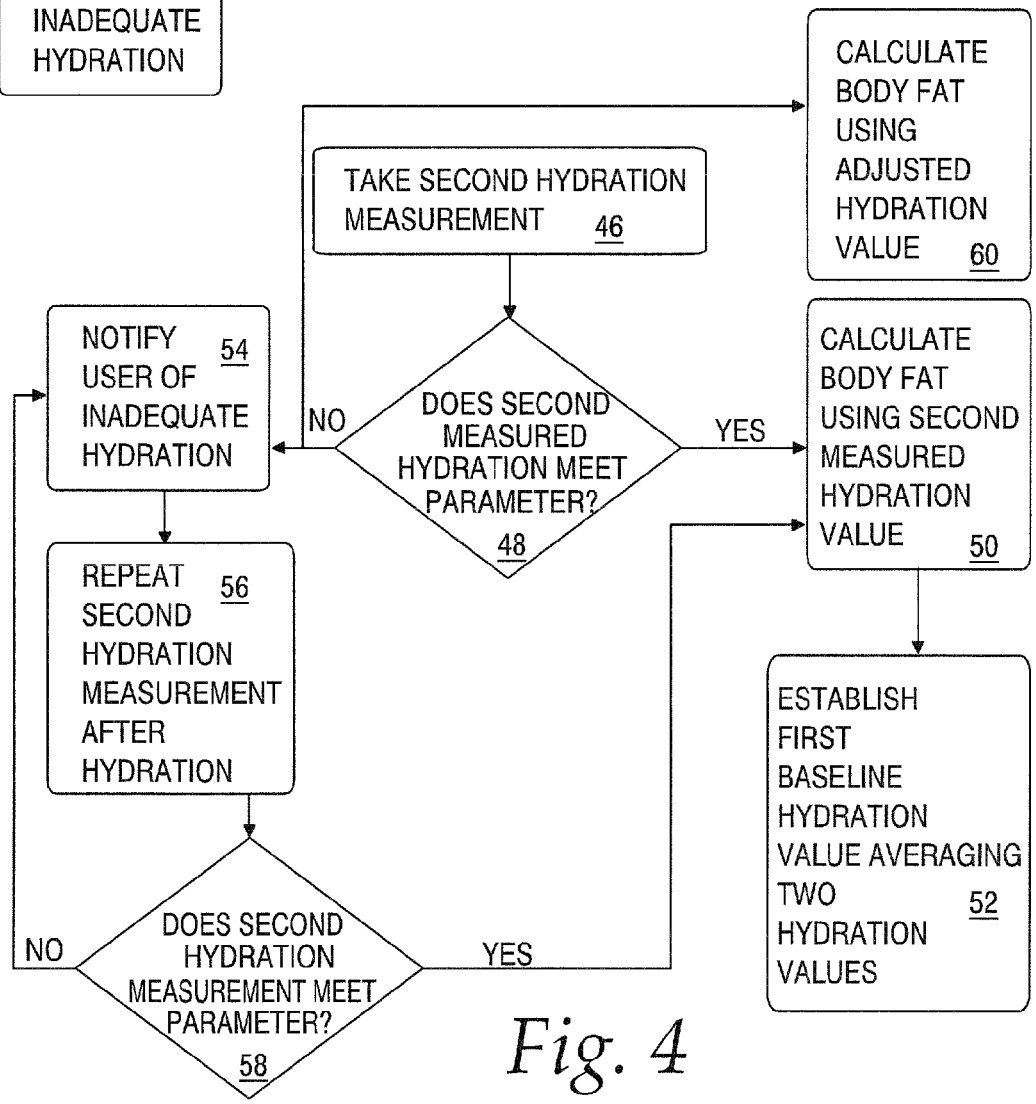
FIG. 4 is a flow diagram representation as in FIG. 3 based upon a second hydration measurement value.

As shown in FIG. 4, a subsequent second hydration measurement is taken using the apparatus 22, as shown at block 46. The system 22 compares the second measured hydration value to the same or a different parameter, as indicated at block 48. With the 75% hydration rate used, if the second measured hydration value is at or greater than 75%, that value is used to calculate body fat through the means 30, as indicated at block 50. At the same time, the apparatus 22 is configured to establish a first baseline hydration value that averages the first two hydration values that are processed by the means 30 in calculating body fat, as shown at block 52.

If the second measured hydration value is not at 75% or greater, the system 22 notifies the user of inadequate hydration, as shown at block 54. As shown at block 56, the second hydration measurement is repeated after hydration. As shown at block 58 if, after hydration, the second hydration measurement does not reach or exceed 75%, the user is so notified, as indicated at block 54 and the cycle repeats until a hydration level of 75% or greater is measured. At that point, the second hydration measurement value can be processed by the means 30, as shown at block 50.

FIG. 4 depicts two different options for apparatus operation. That is, if the second measured hydration value is lower than the established parameter, a user can be forced to hydrate to eventually generate a reading that is a more accurate reflection of body hydration. As a further alternative, as shown at block 60, the body fat percentage can be calculated using an adjusted hydration value, such as the aforementioned 75% value.

Figure 5:
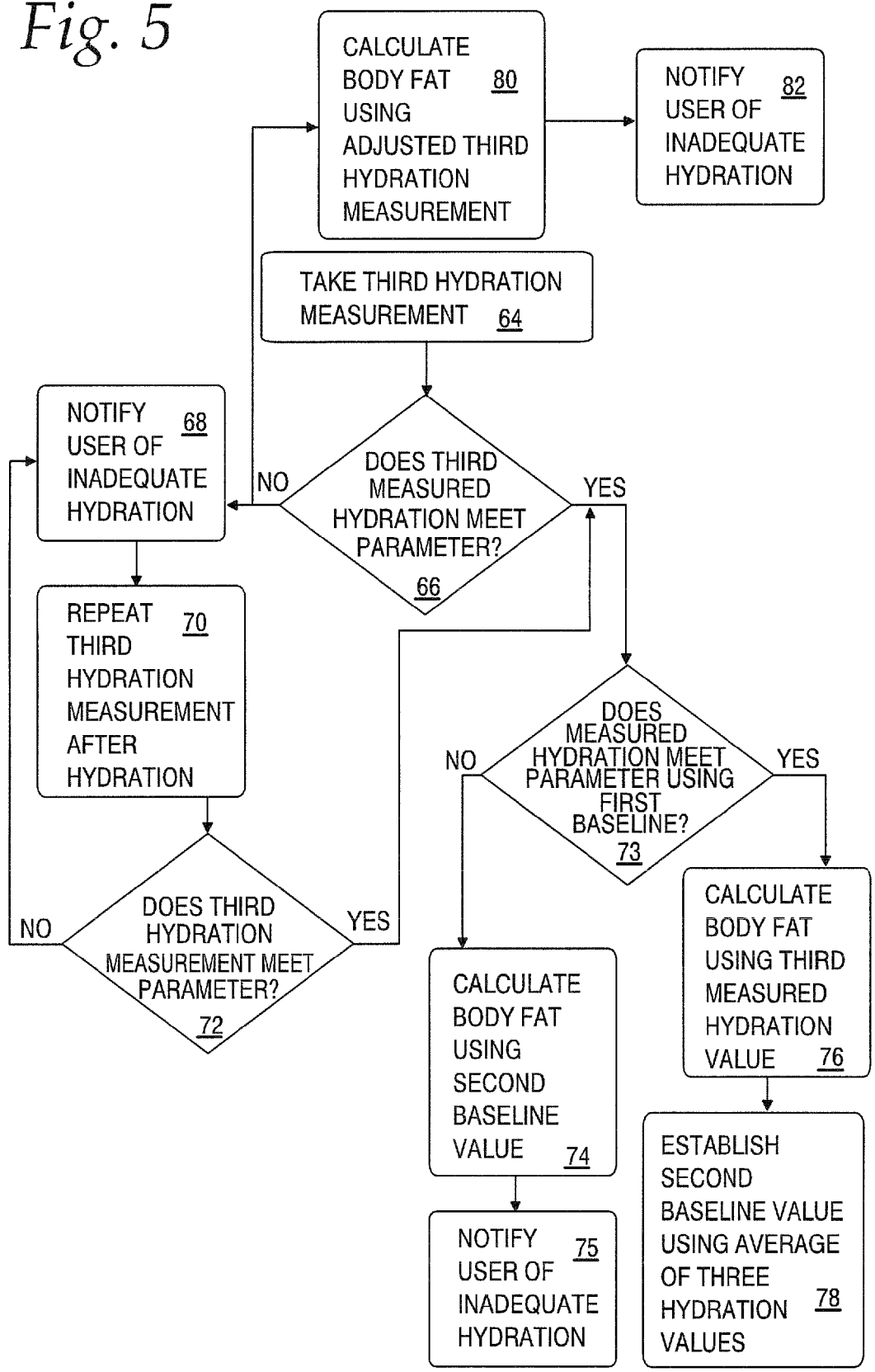
FIG. 5 is a flow diagram representation as in FIG. 3 based upon a third hydration measurement value.

In FIG. 5, system operation is shown for taking a third hydration measurement using the apparatus 22, as shown at block 64. As shown at block 66, it is determined whether the third measured hydration value meets a parameter, which may be the 75% hydration level or the first baseline hydration value that results from averaging as shown in FIG. 4.

If the third measured hydration value does not meet the parameter, as shown at block 68, the user is notified of inadequate hydration. As shown at block 70, the third hydration measurement step may be repeated after hydration. As shown at block 72, if, after hydration, the third hydration measurement value does not meet the established parameter, the user may be notified of inadequate hydration as at block 68 and the cycle repeated until the parameter is met. Once the parameter is met, as shown at block 73, the system may determine whether the parameter using the first baseline hydration value is met. If not, as shown at block 74, the system may calculate the body fat percentage using the second baseline hydration value. As shown at block 75, the user is also notified of inadequate hydration.

If the measured hydration value meets the parameter, as shown at block 76, body fat percentage is calculated using the third measured hydration value. As shown at block 78, the system also establishes a second baseline value using the average of three hydration values that are actually measured, or more preferably processed by the means 30 in prior measurements.

As a further alternative, in the event that the third measured hydration value does not meet the parameters noted at block 66, as shown at block 80, the body fat percentage may be calculated using an adjusted third hydration measurement value, which may be 75%, or another value. At the same time, as noted at block 82, the user is notified that he/she is inadequately hydrated.

Figure 6:
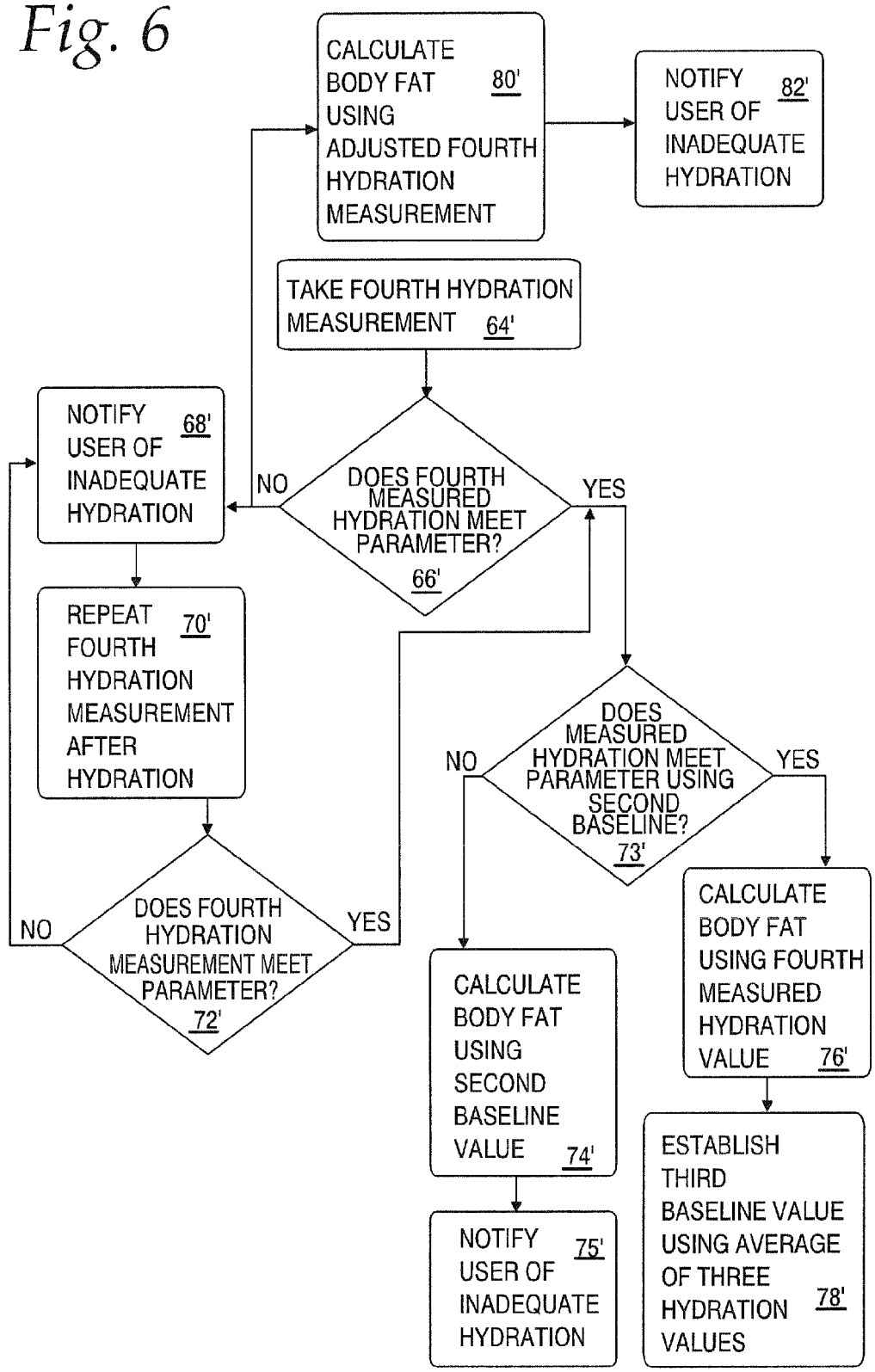
FIG. 6 is a flow diagram representation as in FIG. 3 based upon a fourth hydration measurement value.

In FIG. 6, a flow diagram representation of system operation is shown for taking a subsequent fourth hydration measurement. The blocks in FIG. 6, that correspond to those in FIG. 5, are numbered using the same numbers with a "'" designation. The primary distinction between what is shown in FIGS. 5 and 6 is that in block 78', a third baseline value is established for use as a further parameter and preferably uses less than all of the collection of four prior measurement values. As an example, the first hydration measurement value may be eliminated from the averaging. While this is preferred, any of the four measured hydration values might be eliminated so that only three of the four values are averaged for the recalculated baseline.

As shown in FIG. 7, the means for measuring hydration may include a means 88 for generating instructions to hydrate as the apparatus 22 is utilized as described above. The instructions may be generated by other system components.

As shown in FIG. 8, the means for measuring body fat 30 generates the signal 32 that may be in untranslated form and thus not human readable. A separate conversion means 90 may be provided for converting the signal 32 to a human readable form or another form for subsequent use and/or processing. In the event that the conversion means 90 converts the signal to a human readable form, the translated signal 92 from the conversion means 90 may be made available to a user or another party, as through a display 94.

It should be understood that the precise configuration of the components and their integration is not limited to any specific structure or manner. The aforementioned components could be separate or united into a single instrument.

As one additional variation, as shown in FIG. 9, the inventive system, as shown generically at 96, may have an instrument 98 with a means at 100 for measuring and generating a signal 102 representing a percentage of body fat that is calculated using the aforementioned concept of selectively adjusting measured hydration values.

In this embodiment, the signal 102 is transmitted over a network 104. The network 104 may be a local area network or the internet.

The signal 102 is conveyed to a conversion means/server 106 where appropriate processing may be performed. As an example, the processing may be a conversion of a non-human readable signal to human readable form. Alternatively, the body fat percentage value may be coordinated with a user profile including age, weight, gender, height and lifestyle quantification, as noted above. This feedback may be provided to the user at the instrument location 98 and/or at another location. At the server 106, the data may be stored for future use and comparison purposes. The comparison may involve the user's own data and/or data representative of the general population.

The foregoing disclosure of specific embodiments is intended to be illustrative of the broad concepts comprehended by the invention.

The invention claimed is:

1. A system for measuring percentage of body fat for a user, the system comprising:
   means for measuring body hydration and generating a signal representing a measured hydration value;
   means for selectively changing the measured hydration value to an adjusted hydration value based upon a first parameter to thereby reflect more accurately an actual hydration value for the user, in the event that the user is determined to be dehydrated based upon the first parameter, and generating a signal representing the adjusted hydration value; and
   means for measuring body fat percentage using the signal representing: a) the measured hydration value, in the event that the user is determined not to be dehydrated based upon the first parameter; or b) the adjusted hydration value in the event that the user is determined to be dehydrated based upon the first parameter and the means for selectively changing the measured hydration value changes the measured hydration value based upon the first parameter.

2. A system for measuring percentage of body fat for a user according to claim 1 wherein the means for selectively changing the measured hydration value comprises means for automatically changing the measured hydration value, in the event that the user is determined to be dehydrated, to an adjusted hydration value based upon the first parameter.

3. The system for measuring percentage of body fat for a user according to claim 2 wherein the first parameter comprises a preset minimum hydration value and the means for selectively changing the measured hydration value comprises means for changing the measured hydration value to the preset minimum hydration value in the event that the measured hydration value is below the preset minimum hydration value.

4. The system for measuring percentage of body fat for a user according to claim 3 wherein the means for measuring body hydration comprises means for notifying the user that the user is not properly hydrated in the event that the measured hydration value is below the preset minimum hydration value.

5. The system for measuring percentage of body fat for a user according to claim 3 wherein the preset minimum hydration value is based upon a conventional adequate hydration value derived from a general population analysis.

6. The system for measuring percentage of body fat for a user according to claim 3 wherein the preset minimum hydration value is a baseline hydration value derived from a plurality of prior hydration measurements used by the means for measuring body fat percentage for the user.

7. The system for measuring percentage of body fat for a user according to claim 6 wherein the baseline hydration value is derived by using at least two prior hydration values for the user used by the means for measuring body fat percentage.

8. The system for measuring percentage of body fat for a user according to claim 7 wherein the two prior hydration values are successive hydration values used by the means for measuring body fat percentage.

9. The system for measuring percentage of body fat for a user according to claim 6 wherein the baseline hydration value is derived by averaging a plurality of prior hydration values used by the means for measuring body fat percentage.

10. The system for measuring percentage of body fat for a user according to claim 6 wherein the baseline hydration value is derived by averaging at least two and less than all prior hydration values from a collection of prior hydration values used by the means for measuring body fat percentage in the collection of prior hydration values.

11. The system for measuring percentage of body fat for a user according to claim 1 wherein the system further comprises a display for identifying user body fat percentage as measured by the means for measuring body fat in a human readable form.

12. The system for measuring percentage of body fat for a user according to claim 11 wherein the means for measuring body fat percentage generates a signal in non-human readable form representing measured body fat percentage and the system further comprises a conversion means for changing the signal representing body fat percentage from non-human readable form into a human readable form.

13. The system for measuring percentage of body fat for a user according to claim 12 wherein the means for measuring hydration, means for measuring body fat, and display are at a first location and the conversion means is at a second, remote location.

14. The system for measuring percentage of body fat for a user according to claim 12 wherein the means for measuring hydration, means for measuring body fat, and display are all at the same location.

15. The system for measuring percentage of body fat for a user according to claim 13 wherein the signal representing measured body fat percentage is conveyed to the conversion means over one of a local area network or the internet.

16. The system for measuring percentage of body fat for a user according to claim 15 wherein the means for measuring hydration, means for measuring body fat, and display are combined into an instrument at the first location.

17. The system for measuring percentage of body fat for a user according to claim 1 wherein the first parameter comprises a preset minimum hydration value and the means for measuring body hydration comprises means for notifying a user that the user is not properly hydrated as indicated by the fact that a measured hydration value is below the preset minimum hydration value and thereafter sending a signal to the means for measuring body fat percentage only after the means for measuring body hydration has generated a signal representing a second measured hydration value and after the user has been notified that the user is not properly hydrated.

18. The system for measuring percentage of body fat for a user according to claim 6 wherein the means for selectively changing the measured hydration value comprises means for generating a signal representing the measured hydration value used by the means for measuring body fat percentage in the event that the measured hydration value exceeds the baseline hydration value.

19. The system for measuring percentage of body fat according to claim 1 wherein the means for measuring body fat percentage comprises means for measuring body fat percentage based upon a measured electrical resistance.

20. The system for measuring percentage of body fat for a user according to claim 3 wherein the preset minimum hydration value is on the order of 75%.

* * * * *